United States Patent [19]

Sawyer et al.

[11] Patent Number: 5,602,041
[45] Date of Patent: Feb. 11, 1997

[54] FISH SERUM AS A BLOCKING REAGENT

[75] Inventors: Evelyn S. Sawyer; Philip J. Sawyer, both of Kennebunkport, Me.

[73] Assignee: Sea Run Holdings, Inc., Arundel, Me.

[21] Appl. No.: 297,262

[22] Filed: Aug. 26, 1994

[51] Int. Cl.$^6$ ..................................................... G01N 33/53
[52] U.S. Cl. ........................... 436/518; 436/530; 436/531
[58] Field of Search .................................. 436/518, 528, 436/530, 531, 8, 13, 16, 17, 18, 174, 175, 176, 177, 178, 179, 826; 435/975

[56] References Cited

PUBLICATIONS

Harlow et al, "Antibodies A Laboratory Manual", 1988 by Cold Spring Harbor Laboratories pp. 496–497 and 567–569.
Largone et al, Adv. Immunol, 1982, 32:158–251.
Smith et al, J. Aquat. Anim. Health., Mar. 1993, 5(1):23–35.
Meador et al, National Cancer Instituite Monograph, 65, pp. 211–216 May 1984.
Tutz, "Textbook of Clinical Chemistry" 1986 by W. B. Saunders Company; Philadelphia.
Fischer Scientific Catalogue, pp. 760 and 517, 1991–1992.

*Primary Examiner*—Marianne P. Allen
*Assistant Examiner*—Patricia A. Duffy
*Attorney, Agent, or Firm*—Rabin & Champagne

[57] ABSTRACT

Method of extracting fish serum and using the fish serum as a blocking reagent for solid phase immunoassays. The donor fish for the serum are taken from domesticated stocks reared under controlled conditions similar to rearing conditions for herds of domestic land animals. Control of genetics, habitat, diet, and reproductive status of the donor fish permits reproducibility of results and also provides batch-to-batch consistency in serum taken from the fish.

21 Claims, No Drawings

FISH SERUM AS A BLOCKING REAGENT

FIELD OF THE INVENTION

The present invention relates generally to blocking agents for solid phase immunoassays. In particular, the present invention relates to a method of using serum from cultured fishes as a blocking reagent for solid phase immunoassays such as enzyme-linked immunosorbent assays (ELISA), immunoblotting, and immunohistochemical techniques.

BACKGROUND OF THE INVENTION

Solid phase immunoassays involve the immobilization of biomolecules, primarily proteins, to a surface (e.g., polystyrene, nitrocellulose) via passive or covalent interactions. However, non-specific binding (NSB) of other proteins or biomolecules to non-occupied spaces on the surface during the subsequent steps of the assay is detrimental to the specificity and sensitivity of the assay results. This NSB can be minimized by saturating these non-occupied sites with a blocking reagent, a collective term used to mean various substances that are used to reduce NSB and have no active part in the immunochemical reactions of the assay. Another function of blocking reagents is to stabilize the specifically bound biomolecules and prevent denaturation that can result in loss of immunological or enzymatic activity.

The two classes of blockers now in use for immunoassay are detergents and proteins (Batteiger, 1988).

Non-ionic detergents inhibit non-specific hydrophobic binding to surfaces; they are considered non-permanent blockers since they do not attach to the surface and their effectiveness can be nullified by washing the surface with water or buffers. Non-ionic detergent blockers are typically used only in conjunction with protein blockers.

Proteins are a class of blocking reagents that inhibit both non-specific protein-surface interactions, and protein-protein interactions. They are considered permanent blockers since they attach to the surface. Typical protein blockers include whole normal, pre-immunization mammalian serum, bovine serum albumin (BSA), non-fat dry milk, and fish gelatin (collagen).

Immunological blockers are usually taken from mammalian species such as cattle or goats for most mammalian immunoassays. Prior use of fish products as blockers and stabilizers has been confined to fish gelatin (Norland, 1986). This is derived or processed from collagen, a single protein found in the skin of the carcasses of codfish and other species, usually taken from fish processing plants. Collagen is a structural protein, and is not a component of fish serum.

All of the above blockers have disadvantages that lead to assay problems such as false negative and false positive test results. These factors are summarized below in Table 1.

TABLE 1

Advantages and Disadvantages of Major Blocking Reagents

| Reagent | Advantage | Disadvantage |
| --- | --- | --- |
| Non-fat dry milk | Inexpensive<br>Low Covalent NSB<br>Protein A compatible<br>Low cross-reactivity | Deteriorates rapidly<br>Quality varies<br>Masks some antigens<br>Cross-reacts with anti-DNA antibodies |
| BSA | Inexpensive<br>Low protein-surface NSB | May not be fatty-acid free<br>Quality varies |
| | Well documented<br>Protein A compatible | Single protein/high covalent NSB<br>Cross-reacts with antibodies to BSA-haptens |
| Fish gelatin | Inexpensive<br>Low-protein-protein NSB<br>Protein A compatible | Severely masks antigens<br>Quality varies greatly<br>Inadequate when used alone |
| Mammalian serum | Low protein-surface NSB<br>Low covalent NSB<br>Low protein-protein NSB<br>Stabilizes protein | Expensive<br>Incompatible with Protein A<br>Cross-reacts with anti-IgG antibody |

As shown, the use of mammalian sera or sera components as a blocking reagent can cause cross-reactions in immunoassays that employ other mammalian-derived reagents. The use of fish serum, because of its non-mammalian origin, limits cross-species reactivity.

Although the qualities needed in a blocker may differ somewhat for different applications, the ideal blocker would:

1. Inhibit non-specific binding (NSB) of assay components to the surface including non-specific hydrophobic, ionic, and covalent binding;

2. Inhibit non-specific protein-protein interactions;

3. Exhibit no cross-reactivity with assay components, especially antibodies and Protein A;

4. Minimize effects of protein denaturation that occur with phase transitions associated with immobilization and/or drying;

5. Act as a stabilizer for proteins when used in the diluent of reagents that are stored refrigerated or frozen;

6. Exhibit low enzyme activity (i.e. peroxidase, alkaline phosphatase); and

7. Not disrupt the bonds that immobilize the specific protein or biomolecule.

In addition, the ideal blocker must be free of infectious agents, and must have consistent, reproducible performance.

Because of the wide phylogenetic differences between fishes and mammals, fish serum would seem an unlikely substitute for mammalian serum to those skilled in the art. Indeed, a review of the literature on mammalian immunoassay shows no attempt to employ fish serum as a blocker. Thus, although serum from cultured fishes exhibits many of the qualities of the ideal blocker, any method for using fish serum to stabilize immunologically active reagents, and block nonspecific reactions in mammalian immunoassays remains novel. Fish serum has also not been used previously because uniform populations of fish and methods for production of large pools of high quality serum from these fish have not been available.

SUMMARY OF THE INVENTION

It is therefore an object of the present invention to develop a blocker for mammalian immunoassays that does not result in false positive results due to insufficient surface coverage by the blocker.

It is a further object of the present invention to develop a blocker for mammalian immunoassays that does not result in false positive results due to cross-reactivity with mammalian antibodies.

It is a further object of the present invention to develop a blocker for mammalian immunoassays that does not result in false positive results due to cross-reactivity with Protein A.

It is another object of the present invention to develop a blocker that does not produce false negative results by the masking of specifically-bound biomolecules such that their conformation and reactivity is compromised.

It is another object of the present invention to develop a blocker that does not produce false negative results by the disruption of the binding forces that immobilize the specifically-bound molecules such that their conformation and reactivity is compromised.

It is another object of the present invention to develop a blocker that does not produce false negative results by the lack of stabilizing effect on specifically-bound molecules such that their conformation and reactivity is compromised.

It is still a further object of the present invention to provide a serum blocking reagent with components that are highly soluble at room temperature and at temperatures below which most immunoassays are performed.

It is yet another object of the present invention to provide a serum that is free from mammalian infectious organisms that could contaminate assays or endanger laboratory personnel.

It is a further object of the present invention to provide a method or process whereby serum from cultured fish can be used as a blocker and stabilizer in mammalian immunoassays.

It is an additional object of the present invention to provide a fish serum blocking reagent with a lot-to-lot consistency and low variability that would not be possible in serum from wild fishes.

It is a further object of the present invention to provide a fish serum blocking reagent that eliminates cross-reactivity of the blocking reagent molecules with other reagent molecules.

These and other objects and advantages of the present invention will be apparent to those of ordinary skill in the art upon inspection of the detailed description, drawings, and appended claims.

As previously noted, mammalian, whole normal, or pre-immune serum is typically the blocking reagent of choice for many immunoassays. The logic of this choice is that normal serum contains a wide variety of biomolecules (proteins, glycoproteins, glycolipids) of various molecular weights and configurations such that hydrophobic, ionic, and covalent active sites on the surface can be blocked adequately. Fish serum, like mammalian serum, contains a wide variety of biomolecules and thus prevents NSB in the same efficient manner. However, as explained below, compared to mammalian serum, fish serum is a superior blocker.

In evolutionary terms, the fishes are a distinct and remote group from mammals. Unlike mammalian sera, IgG (or similar antibody glycoproteins) are absent in fish serum. The major class of fish antibody is a tetrameric protein with a structure similar (but not cross-reactive) with the IgM pentamer of mammals. Therefore, fish serum shows little cross-reactivity with mammalian anti-IgG antibodies.

Most immunoassays use a labeled (enzyme, fluorescent, radioactive) anti-IgG antibody to detect bound anti-antigen IgG because of the convenience and availability of these anti-IgG antibodies. Therefore, it is important that the blocking reagent not exhibit any cross-reactivity with the anti-IgG antibody being employed in the assay. This cross-reactivity can be avoided by using a blocker from an evolutionarily distant species. Fish serum shows little or no cross-reactivity with a wide range of anti-IgG antibodies produced against mammalian IgGs.

The absence of IgG molecules affords fish serum the advantage of exhibiting little or no cross-reactivity with Protein A. Protein A is a 42,000 dalton polypeptide that is a normal constituent of the cell wall of *Staphylococcus aureus*. Protein A binds to the Fc portion of several different classes and subclasses of antibodies; however, binding affinity is greatest for IgG and its subclasses. Labeled (enzyme, fluorescent, radioactive) Protein A is typically used to detect monoclonal antibodies to specific antigens that are bound to a surface. This type of assay requires that the blocking agent show no detectable cross-reactivity with Protein A.

The temperature range of most fish serum is lower than that of mammals since their body temperature approximates the water temperature rather than 37° C. (human body temperature). This means that the solubility of fish serum components is optimal at ambient (room) temperature where most assays are performed.

Fishes are cold-blooded vertebrates whose body temperature approximates the waters where they live. Cold-water fishes such as the salmon and trout normally live in water with temperatures between 0° C. and 18° C., 20° C. below the body temperature of most mammals. Therefore, there are few if any fish pathogens that infect mammals. This eliminates many of the contamination problems such as viruses and mycoplasma found in mammalian sera.

Also of great importance is the issue of human safety in biological testing. Mammalian sera are usually screened for infectious organisms, but a serious cause for concern is the all-protein agent called a prion for which no test is available. This organism causes a fatal brain disease in cattle, Bovine Spongiform Encephalopathy (BSE). Similar spongiform encephalopathies occur in sheep, goats, and other mammals, and there is some evidence that the disease can be transmitted to humans (Marsh, 1993). In humans, the closely related disease is called Kreutzfeld-Jacob disease or "kuru".

Therefore, the use of fish serum as a blocker provides safety from BSE, or other infectious agents, for laboratory personnel.

Fish serum is a material that is entirely different than fish gelatin. Unlike the single protein fish gelatin, fish serum contains a wide variety of biomolecules comparable to those in mammalian serum but with low cross-reactivity with mammalian antibodies.

The composition of fish serum used in the present invention is controlled and consistent. Since fish gelatin is a by-product of fish processing, the source of the gelatin is wild fish which vary in diet, habitat, and other factors. Many species of fishes from many locations may be used. Therefore, product variability is high, and blocking efficiency is unpredictable.

In contrast to the wild fishes used as a source of fish gelatin, donor fish for serum are taken from domesticated stocks reared under controlled conditions similar to rearing conditions for herds of domestic land animals. This control of genetics, habitat, diet, and reproductive status permits reproducibility and batch-to-batch consistency in serum from these cultured fishes.

As a blocker, fish serum performs quite differently than fish gelatin. Fish gelatin, a single protein product, lacks the versatility to block hydrophobic, ionic, and covalent active sites on surfaces (Vogt et al., 1987). Typically, hydrophobic areas on surfaces are left unblocked when fish gelatin is used as the sole blocking reagent, therefore a second blocker is needed. Fish gelatin tends to block protein-protein interactions, and can interfere with specific antigen-antibody reactions by masking the surface-bound biomolecule, thereby reducing sensitivity and producing false-negative test results. Fish serum stabilizes protein conformation without interfering with antigen-antibody or receptor-ligand reactions.

DETAILED DESCRIPTION OF THE PRESENT INVENTION

The process begins with the donor fish from which blood is extracted. These fish should be taken from a single domesticated stock of known genetic background, and reared under the controlled conditions of aquaculture facilities. The essential requirement is for donor fish to be reared under consistent and reproducible conditions, not necessarily the nature or specifics of these conditions. For example, in certain blocking applications, a low-lipid serum is desirable. Therefore fish must be starved before bleeding. For applications where sex steroids must be absent in serum, triploidy can be induced in donor fish. To insure reproducibility and lot-to-lot consistency of serum, factors such as genetics, diet, habitat, reproductive status, and other controllable conditions and aspects of genetic background must be under human control similar to that of land-based herds.

Donor fish used as a serum source in the present invention were the species *Salmo salar*, the Atlantic salmon, and *Oncorhynchus mykiss*, the rainbow trout or steelhead. These species were chosen because consistent and reproducible methods for their production are well-established, large numbers of these species are produced in aquaculture facilities, and they grow to a large enough size (over a kilogram) so that blood can be obtained easily. Other species of cultured fish also fit these criteria, such as catfish, striped bass and sturgeon, and *tilapia*. Other species of cultured fish may be used as well.

Donor fish used in developing the present invention were 1. progeny of a single domesticated broodstock, 2. inspected for fish disease according to the American Fisheries Society "Blue Book" standards, 3. sexually immature, and 4. larger than one kilogram. All fish were reared by standard husbandry methods appropriate to the species (Piper et al, 1988) in freshwater raceways or seawater net-pens. They were fed a commercial salmonid feed with a composition consistent with that recommended for each species (Halver, 1972). Fish were starved for up to 48 hours before bleeding to reduce serum lipids, especially free fatty acids. These could oxidize upon immobilization, and cause ionic and hydrophobic (lipophilic) interactions non-specifically, all within the same molecule.

Water temperature at the time of bleeding ranged from about 4° C. to about 16° C. This temperature range is not essential for serum quality, but is a consideration in avoiding handling stress on the fish. Each fish is stunned by a blow to the head, is immersed in ice-water, or is anesthetized in water containing $CO_2$ or other fish anesthesia. The objective is to stun the fish to a level of loss of reflex reactivity.

Whole blood is withdrawn, preferably by syringe or vacuum tube, from the caudal artery or vein. Blood is allowed to clot at room temperature for not less than about 15 minutes or no more than about 2 hours, and is then centrifuged at 1100 g for at least about 10 minutes and for no more than about 20 minutes, so that the serum is separated from the cells.

After centrifugation, serum is removed from the collection tubes, and is tested for the presence of peroxidase by the Worthington enzyme assay method (Worthington Biochemical, 1994), and is then filter-sterilized by passing through a 0.45 micron filter and then through a 0.22 micron pore-size membrane filter.

Serum taken from the described group of fish on the same day is considered a single lot. This lot is packaged in 50 or 100 ml sterile polyethylene bottles and frozen at −70° C.

Fish serum is used as a blocking reagent in the following manner. An antigen, antibody, receptor, ligand, or other biomolecules is passively or covalently immobilized on a surface. Examples of well known surfaces appropriate for such use are polystyrene and nitrocellulose, although other surfaces are known and used by those of ordinary skill in the art. Prior to specific coupling of the bound biomolecule with its complementary component (antigen-antibody), non-occupied sites on the surface must be blocked with an inert, non-reactive reagent. Fish serum is used as this reagent. The frozen fish serum is thawed at room temperature and diluted in an appropriate physiological buffer. The fish serum may be diluted in the buffer to a concentration of between about 2 percent and about 20 percent, although the preferred level of dilution is about 10 percent. Examples of well known physiological buffers appropriate for such use are phosphate buffered saline and carbonate buffer. The actual buffer used depends on the particular biomolecule being immobilized and on the surface used. Other buffers are known and used by those of ordinary skill in the art, and the choice of which buffer(s) is appropriate for use in a particular case is determinable by one of ordinary skill in the art.

The resulting solution is mixed well to ensure homogeneity. The diluted fish serum solution is added to the surface at a volume of from at least about 1.5 times the volume of biomolecule immobilized, in order to ensure adequate blocking. It is preferred that the volume of diluted fish serum solution range from about 1.5 to about 2 times the volume of biomolecule.

The combination of surface, biomolecule, and blocker is then incubated for a length of time depending on the surface area and on the surface type being blocked. Incubation normally lasts from about 5 to about 30 minutes, although the time period may be longer if the surface area is great, possibly lasting over night. The temperature of incubation varies from case to case, depending on the type of assay. Typical incubation temperatures may range from 4° C. to 37° C. The three typical "benchmark" temperatures used are 4° C., room temperature (20° C. to 25° C.), and 37° C. Room temperature is the most often used among the three; 4° C. is the temperature usually used over long incubation periods. After the incubation is complete, any excess blocking solution is removed from the surface, usually by decanting or by aspiration.

At this point, the remainder of the assay can be performed, or the blocked surface can be dried and stored at 4° C. for later use. The remainder of the assay consists of the specific coupling of analytes to the immobilized antigen, antibody, receptor, ligand, or other biomolecule, and the detection of specific coupling through the use of markers such as radioactive, fluorescent, colorimetric, and chemiluminescent markers.

Preferred and alternate embodiments of the present invention have now been described in detail. It is to be noted, however, that this description of these specific embodiments is merely illustrative of the principles underlying the inventive concept. It is therefore contemplated that various modifications of the disclosed embodiments will, without departing from the spirit and scope of the invention, be apparent to persons skilled in the art.

REFERENCES

Batteiger, B. E., "Blocking of Immunoblots", *Handbook of Immunoblotting of Proteins*, O. J. Bjerrum and N. H. Heegaard (Eds.) 1988, CRC Press, Boca Raton, Fla.

Halver, J. E., *Fish Nutrition*, 1972, Academic Press, New York, 713 pp.

Marsh, R. F., Symposium on risk assessment of the possible occurrence of bovine spongiform encephalopathy in the United States, 1993, JAVMA 204(1): 70–74.

Norland, R., "Fish Gelatin: Technical Aspects and Applications", Special Report, 1986, Norlands Products, Inc., New Brunswick, N.J.

Piper, R. G., McElwain, I., Orme, L. E., McCraren, J. P., Fowler, L. G., and Leonard, J. R., *Fish Hatchery Management*, 1983, U.S. Department of the Interior, Fish and Wildlife Service, Washington, D.C., 517 pp.

Vogt, R. F., Phillips, D. L., Henderson, O., Whitfield, W., and Spierto, F. W., "Quantitative Differences Among Various Proteins as Blocking Agents for ELISA Microtiter Plates", *Journal of Immun. Methods* 101: 43–50, 1987.

What is claimed is:

1. A method of using a blocking reagent in an immunoassay process, comprising:
   a. immobilizing biomolecules to a surface; and
   b. saturating non-occupied sites on the surface with a blocking reagent; wherein
   c. the blocking reagent comprises fish serum.

2. The method of claim 1, further comprising:
   diluting the fish serum in a physiological buffer to form a fish serum solution;
   mixing the fish serum solution until the fish serum solution is substantially homogeneous;
   adding the fish serum solution to the surface as a blocking reagent;
   incubating the surface, immobilized biomolecules, and blocking reagent; and
   removing excess blocking reagent from the surface.

3. The method of claim 1, wherein the fish serum is obtained by:
   a. raising fish such that controllable conditions and genetic background of the fish remain substantially constant and reproducible;
   b. starving the fish for up to about forty-eight hours;
   c. stunning the fish by non-toxic methods until the fish is unconscious;
   d. withdrawing whole blood from the fish;
   e. allowing the whole blood to clot;
   f. centrifuging the blood until serum is separated from cells;
   g. removing the serum; and
   h. sterilizing the serum.

4. A method of using fish serum as a blocking reagent, comprising immobilizing biomolecules on a surface and saturating non-occupied sites on the surface with a blocking reagent, the blocking reagent comprising thawed fish serum, wherein the fish serum is prepared by:
   a. raising fish such that controllable conditions and genetic background of the fish remain substantially constant and reproducible;
   b. starving the fish for up to about forty-eight hours;
   c. stunning the fish by non-toxic methods until the fish is unconscious;
   d. withdrawing whole blood from the fish;
   e. allowing the whole blood to clot;
   f. centrifuging the blood until serum is separated from cells;
   g. removing the serum;
   h. sterilizing the serum; and
   i. freezing the serum.

5. The method of claim 4 wherein allowing the whole blood to clot lasts for a duration of from about fifteen minutes to about two hours.

6. The method of claim 4 wherein centrifuging the blood occurs at 1100×g for at least ten minutes.

7. The method of claim 4 wherein freezing the serum includes reducing the temperature of the fish serum to −70 degrees C.

8. The method of claim 4 wherein the fish used as a source of blood are selected from the group of fish consisting of *Oncorhynchus mykiss* and *Salmo salar*.

9. The method of claim 4, wherein centrifuging the blood takes place for at least about ten minutes and for no longer than about twenty minutes.

10. The method of claim 4 wherein sterilizing the serum comprises filter sterilizing the serum.

11. The method of claim 10 wherein sterilizing the serum comprises:
    a. filtering the serum through a 0.45 micron filter; and
    b. filtering the serum through a 0.22 micron filter.

12. The method of claim 4, wherein immobilizing biomolecules on a surface and saturating non-occupied sites on the surface with a blocking reagent comprises:
    a. immobilizing a group of biomolecules on a surface;
    b. thawing the serum and diluting the serum in a physiological buffer to form a fish serum solution;
    c. mixing the fish serum solution until the fish serum solution is substantially homogeneous; and
    d. adding the fish serum solution to the surface as a blocking reagent.

13. A method of using a blocking reagent in an assay process, comprising:
    a. immobilizing a group of biomolecules on a surface;
    b. diluting fish serum in a physiological buffer to form a fish serum solution;
    c. mixing the solution until the solution is substantially homogeneous;
    d. adding the fish serum solution to the surface as a blocking reagent;
    e. incubating the surface, immobilized molecules, and blocking reagent; and
    f. removing excess blocking reagent from the surface.

14. The method of claim 13, wherein the fish serum is prepared by:
    raising fish such that controllable conditions and genetic background of the fish remain substantially constant and reproducible;
    selecting sexually immature fish;

starving the selected fish for up to about forty-eight hours;

stunning the starved fish by non-toxic methods until the fish is unconscious;

withdrawing whole blood from the unconscious fish;

allowing the whole blood to clot;

centrifuging the blood until serum is separated from cells;

removing the serum; and sterilizing the serum.

15. The method of claim 13, wherein the assay further comprises coupling analytes to the immobilized biomolecules and detecting specific coupling through the use of markers.

16. The method of claim 13, wherein the fish serum is diluted to a concentration ranging from about two percent to about twenty percent.

17. The method of claim 13, wherein the physiological buffer is selected from the group of buffers consisting of phosphate buffered saline and carbonate buffer.

18. The method of claim 13, wherein the amount of fish serum solution added to the surface is at least 1.5 times the volume of biomolecules immobilized on the surface.

19. The method of claim 13, wherein the biomolecules immobilized are selected from the group of biomolecules consisting of antigens, antibodies, receptors, and ligands.

20. The method of claim 13, wherein the surface on which the biomolecules are immobilized is made of a material selected from the group of materials consisting of polystyrene and nitrocellulose.

21. The method of claim 13, wherein incubation of the surface, biomolecules, and blocking reagent takes place at a temperature ranging from about 4° C. to about 37° C. for a time period of no less than about five minutes.

* * * * *